US007758861B2

(12) United States Patent
Rajagopalan et al.

(10) Patent No.: US 7,758,861 B2
(45) Date of Patent: Jul. 20, 2010

(54) DYE-SULFENATES FOR DUAL PHOTOTHERAPY

(75) Inventors: Raghavan Rajagopalan, Beechwood, OH (US); Samuel I. Achilefu, St. Louis, MO (US); Joseph E. Bugaj, St. Charles, MO (US); Richard D. Dorshow, St. Louis, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 0 days.

(21) Appl. No.: 11/277,057

(22) Filed: Mar. 21, 2006

(65) Prior Publication Data
US 2006/0177457 A1 Aug. 10, 2006

Related U.S. Application Data (63) Continuation of application No. 09/898,809, filed on Jul. 3, 2001, now Pat. No. 7,351,807.

(51) Int. Cl.
*A61K 41/00* (2006.01)
*C09B 17/00* (2006.01)
*C09B 19/00* (2006.01)
*C09B 23/00* (2006.01)
*C09B 47/00* (2006.01)
*C09B 57/00* (2006.01)
*C07D 311/82* (2006.01)
*C07C 313/08* (2006.01)

(52) U.S. Cl. ............... 424/178.1; 514/150; 514/185; 514/224.8; 514/226.2; 514/369; 514/410; 514/419; 530/391.1; 530/409; 534/727; 540/140; 540/145; 544/37; 544/38; 544/46; 548/181; 548/182; 548/465

(58) Field of Classification Search .......... 544/37, 544/38, 46; 514/224.8, 226.2
See application file for complete search history.

(56) References Cited

U.S. PATENT DOCUMENTS

| 2,929,824 | A | 3/1960 | Kharasch et al. |
| 5,518,888 | A | 5/1996 | Waldman |
| 5,714,342 | A | 2/1998 | Komoriya et al. |
| 7,230,088 | B2 | 6/2007 | Rajagopalan et al. |
| 7,267,994 | B2 | 9/2007 | Meares et al. |
| 7,303,926 | B2 | 12/2007 | Rajagopalan et al. |
| 7,427,657 | B1 * | 9/2008 | Rajagopalan et al. ....... 530/324 |
| 2003/0036538 | A1 | 2/2003 | Rajagopalan et al. |
| 2004/0156783 | A1 | 8/2004 | Rajagopalan et al. |
| 2006/0105974 | A1 | 5/2006 | Lange et al. |
| 2006/0177457 | A1 | 8/2006 | Rajagopalan et al. |

FOREIGN PATENT DOCUMENTS

| WO | WO 00/41727 | 7/2000 |
| WO | WO 03/004466 | 1/2003 |

OTHER PUBLICATIONS

Kreimer-Birnbaum, Modified Porphyrins, Chlorins, Phthalocyanines, and Purpurins: Second-Generation Photosensitizers for Photodynamic Therapy, Seminars in Hematology, vol. 26, No. 2 (Apr. 1998), pp. 157-173 XP 000501369.
Delaney et al., Photodynamic Therapy of Cancer, Comprehensive Therapy, 1988, vol. 14, No. 5, pp. 43-55 XP 000909044.
Pasto et al., Photolysis of Alkyl 4-Nitrobenzenesulfenates. A New and Versatile method for the Generation of Free Radicals, J. Org. Chem., 1990, vol. 55, pp. 5815-5816 XP 002353156.
Achilefu et al., Novel Receptor-Targeted Fluorescent Contrast Agents for In Vivo Tumor Imaging, Investigative Radiology, vol. 35, No. 8, 2000, pp. 479-485.
Amaudrut et al., The Thermal Sulfenate-Sulfoxide Rearrangement: A Radical Pair Mechanism, J. Amer. Chem., Soc., vol. 122, 2000, pp. 3367-3374.
Andreoni et al., Tumour photosensitization by chemotherapeutic drugs, Biology, N3, 1993, pp. 43-46.
Ballou et al., Tumor labeling in vivo using cyanine-conjugated monoclonal antibodies, Cancer Immunology and Immunotherapy, vol. 41, 1993, pp. 257-263.
Dougherty et al., Photoradiation Therapy. II. Cure of Animal Tumors with Hematoporphyrin and Light, Journal of the National Cancer Institute, vol. 55, No. 1, 1975, pp. 115-121.
Freiherr, The Light Suff: Optical Imaging in Medical Diagnosis, Medical Device & Diagnostic Industry Magazine, 1998, pp. 1-7.

(Continued)

*Primary Examiner*—Fiona T Powers
(74) *Attorney, Agent, or Firm*—Thompson Hine LLP (57) ABSTRACT

The present invention discloses dye-sulfenate derivatives and their bioconjugates for dual phototherapy of tumors and other lesions. The compounds of the present invention may contain either a mixture of Type 1 and Type 2 agents or a single entity that integrates both units in the same molecules. The compounds are designed to produce both Type 1 and Type 2 phototherapeutic effect at once using dual wavelength light source that will produce singlet oxygen and free radicals at the lesion of interest.

22 Claims, 2 Drawing Sheets

OTHER PUBLICATIONS

Hamblin et al., On the mechanism of the tumour-localising effect in photodynamic therapy, J. Photochem. Photobiol. B: Biol., vol. 23, 1994, pp. 3-8.

Hebeden et al., Diagnositc Imaging with light, The British Journal of Radiology, vol. 70, 1997 pp. S206-S214.

Hnatowich et al., Radioactive Labeling of Antibody: A Simple and Efficient Method, Science, vol. 220, 1983, pp. 613-615.

Jori, Tumour photosensitizers: approaches to enhance the selectivity and efficiency of photodynamic therapy, Journal of Photochemistry and Photobiology B: Biology, vol. 36, 1996, pp. 87-93.

Jori, Novel Therapeutic Modalities Based on Photosensitized Processes, EPA Newsletter, No. 60, 1997, pp. 12-18.

Jori, Far-red-absorbing photosensitizers: their use in the photodynamic therapy of tumours, J. Photochem. Photobiol. A: Chem., vol. 62, 1992, pp. 371-378.

Korbelik, Photosensitizers in photodynamic therapy, Periodicum Biologorum, vol. 93, No. 4, 1991, pp. 563-574.

Licha et al., New contrast Agents for Optical Imaging: Acid-Cleavable Conjugates of Cyanine Dyes with Biomedicals, Part of the SPIE Conference on Molecular Imaging: Reports, Dyes, and Instrumentation, Proceedings of SPIE, vol. 3600, 1999, pp. 29-35.

Lipson et al., Hematoporphyrin Derivative for Detection and Management of Cancer, Cancer, vol. 20. No. 12, 1967, pp. 2255-2257.

Luo et al., Rapid Initiation of Apoptosis by Photodynamic Therapy, Photochemistry and Photobiology, vol. 63, No. 4, 1996, pp. 528-534.

Matsumura, 1-Aminoacridine-4-carboxylic Acid, Journal of the American chemical Society, vol. 60, 1938, pp. 591-593.

Miller et al., Preclinical Assessment of Hypocrellin b. and Hypocrellin B Derivatives as Sensitizers of Radical in Biology and Medicine, vol. 28, No. 11, 2000, pp. 1589-1597.

Pasto et al., Demonstration of the Synthetic Utility of the Generation of Alkoxy Radicals by the Proto-Induced, Homolytic Dissociation of Alkyl 4-Nitrobenzenesulfenates, Tetrahedron Letters, vol. 35, No. 25, 1994, pp. 4303-4306.

Pelegrin et al., Photoimmunodiagnosis with antibody-fluorescein conjugates: in vitro and in vivo preclinical studies, J. Cell Pharmacol, vol. 3, 1992, pp. 141-145.

Roberts et al., Role of Neovasculature and Vascular Permeability on the Tumor Retention of Photodynamic Agents, Cancer Research, vol. 52, 1992, pp. 924-930.

Stables et al., Photodynamic therapy, Cancer Treatment Reviews, vol. 21, 1995, pp. 311-323.

Takemura et al., Mechanism of Photodynamic Therapy: Exploration by Photophysiocochemical Study, Frontiers of Photobiology, 1993, pp. 503-506.

Trauner et al., Photodynamic Synovectomy Using Benzoporphyrin Derivative in an Antigen-Induced Arthritis Model for Rheumatoid Arthritis, Photochemistry and Photobiology, vol. 67, No. 1, 1998, pp. 133-139.

Van Geel et al., Photosensitizing Efficacy of MTHPC-PDT Compared to Photofrin-PDT in the RIF1 Mouse Tumour and Normal Skin, Int. J. Cancer, vol. 60, 1995, pp. 388-394.

*Estrogen Receptor Competitor Assay Kits, Red*, by Invitrogen https://catalog.invitrogen.com/index.cfm?fuseaction=viewCatalog.view/ProductDetails&pr..., 1 pg.

Alexander, et al., *Guide to Receptors and Channels*, 1st Edition (2005 revision), 6 pgs.

Hagstrom, James E. et al; *Transfection Reagents: High Efficiency and Low Toxicity*; Panvera (Winter 1998)—,4 pgs.

Ute Schafer, et al.; *Binding of Cholecystokinin-8i (CCK-8) Peptide Derivatives to $CCK_A$ and $CCK_B$ Receptors*; Journal of Neurochemistry 1994, 6 pgs.

*The Victor$^3$ Multilable Plate Reader*; Perkin Elmer, 10 pgs.

Vallabhajosula, Vet al.; *Preclinical Evaluation of Technetium-99m Labeled Somatostatin Receptor Binding Peptides*; The Journal of Nuclear Medicine vol. 37, No. 6 Jun. 1996, 7 pgs.

Parker, Gregory J. et al; *Development of High Throughput Screening Assays Using Fluorescence Polarization: Nuclear Receptor-Ligand-Binding and Kinase\*/Phosphatase Assays*; Journal of Biomolecular Screening, vol. 5, 77-88, Nov. 2, 2000, 12 pgs.

Dufes, Christine et al; *Niosomes and Polymeric Chitosan Based Vesicles Bearing Transferrin and Glucose Ligands for Drug Targeting* Pharmaceutical Research, vol. 17, Nov. 10, 2000, 8 pgs.

Tilly, Jonathan L., et al; *Expression of Recombinant Human Follicle-Stimulating Hormone Receptor: Species-Specific Ligand Binding, Signal Transduction, and Identification of Multiple Ovarian Messenger Ribonucleic Acid Transcripts\**; Endocrinology, vol. 131, No. 2, 799-806, 1992, 8 pgs.

International Search Report issued Dec. 30, 2002 regarding International Application No. PCT/US/02/19184 (International Filing Date Jun. 18, 2002) (1532 WO), 3 pgs.

PCT Written Opinion issued Jul. 2, 2003 regarding International Application No. PCT/US/02/19184 (International filing Date Jun. 18, 2002) (1532 WO), 6 pgs.

International Preliminary Report on Patentability issued Dec. 2, 2003 regarding Internatinal Application No. PCT/US/02/19184 (International Filing Date Jun. 18, 2002) (1532 WO), 7 pgs.

Patent Search Report by Cardinal Intellectual Property; Dec. 2007, 14 pgs.

Patent Search Report by Landon IP Inc.; 2008, 17 pgs.

Technical Search Report by PRV InterPat; Jan. 1, 2008, 47 pgs.

Ferreira, Paula M., et al; *Synthesis of Non-Natural Amino Acids from n-(p-Toylsulfonyl)-a,B-didehydroamino Acid Derivatives*; Eur. J. Org. Chem. 2003, 2635-2644, 10 pgs.

Ruano, Jose L. Garcia; *A General and Expeditious One-Pot Synthesis of Sulfoxides in High Optical Purity from Nonephedrine-Derived Sulfamidites*; 2003 American Chemical Society Dec. 14, 2002, 4 pgs.

Ferreira, Paula M., et al; *Synthesis of non proteinogenic amino acids from N-(4-toluenesulfonyl) dehydroamino acid derivatives*; Tetrahedron Letters 43 (2002) 4495-4497, 3 pgs.

Rosen, Oren, et al; *Thiolysis of the 3-nitro-2pyridinesulfenyl (Npys) protecting group*; Int. J. Peptide Protein Res. 35, 1990, 545-549, 5 pgs.

Rosen, O, et al; *3-Nitro-2-Pyridinesulfenyul (Npys): A Versatile Protecting Group in Peptide Synthesis; Department of Organic Chemistry, The Weizmann Institute of Science Rehovot 76100, Israel*, 3 pgs.

Matsueda, Rei, et al; *3-Nitro-2-Pyridinesulfenyl Protecting Group: Activatable Protecting Group For Peptide Synthesis and Enzyme Modification*; Peptide Chemistry 1980 protein Research Foundation, Osaka (1981), 6 pgs.

Matsueda, Rei, et al; *3-Nitro-2-Pyridinesulfenyl (Npys) Group A Novel Selective Protecting Group Which Can Be Activated for Peptide Bond Formation*; Department of Physiology and Biophysics, University of Illinois at the Medical Center, Chicago, Illinois U.S.A. Jun. 18, 1980, 10 pgs.

Matsueda, Rei, et al; *Syntheses of 3-Nitro-2-Phridinesulfenates*; Department of Chemistry, The University of Chicago Heterocycles vol. 15 No. 2, 1981, 3 pgs.

Matsueda, R., et al; *Novel Protecting Group Activated by Tertiary Phosphine For Peptide Synthesis*; University of Illinois at the Medical Center, 4 pgs.

Wudl, Fred, et al; *Asymmetric Sythesis of Chiral Sulfoxides An Intramolecular O—N Sulfinyl Migration*; State University of New Yor at Buffalo, Buffalo New York Dec. 22, 1972, 9 pgs.

Ferreira, Paula M. et al., *Synthesis of non-proteinogenic amino acids from N-(4-toluenesulfonyl) dehydroalanine derivatives*, Peptides 2002, 94-95, 2 pgs.

*Peripheral to the Focus of the Disclosure* (Jan. 16, 2008), 71 pgs.

*Central to the Focus of the Disclosure* (Jan. 16, 2008), 6 pgs.

\* cited by examiner

DYE-SULFENATES FOR DUAL PHOTOTHERAPY

CROSS-REFERENCE TO RELATED APPLICATIONS

This application is a continuation of pending U.S. application Ser. No. 09/898,809, titled Dye-Sulfonates For Dual Phototherapy, filed on Jul. 3, 2001, having the same inventors and assignee as the present invention, said application incorporated herein by reference in its entirety.

FIELD OF THE INVENTION

The present invention relates to novel dye-sulfenate compounds, and to phototherapeutic procedures using these compounds.

BACKGROUND OF THE INVENTION

The use of visible and near-infrared (NIR) light in clinical practice is growing rapidly. Compounds absorbing or emitting in the visible or NIR, or long-wavelength (UV-A, >350 nm) region of the electromagnetic spectrum are potentially useful for optical tomographic imaging, endoscopic visualization, and phototherapy. However, a major advantage of biomedical optics lies in its therapeutic potential. Phototherapy has been demonstrated to be a safe and effective procedure for the treatment of various surface lesions, both external and internal. Its efficacy is akin to radiotherapy, but it advantageously lacks the harmful radiotoxicity to critical non-target organs.

Phototherapy has been in existence for many centuries and has been used to treat various skin surface ailments. As early as 1400 B.C. in India, plant extracts (psoralens), in combination with sunlight, were used to treat vitiligo. In 1903, Von Tappeiner and Jesionek, used eosin as a photosensitizer for treating skin cancer, lupus of the skin, and condylomata of female genitalia. Over the years, the combination of psoralens and ultraviolet A (low-energy) radiation has been used to treat a wide variety of dermatological diseases and manifestations including psoriasis, parapsoriasis, cutaneous T-cell lymphoma, eczema, vitiligo, greata, and neonatal bilirubinemia. Although the potential of cancer phototherapy has been recognized since the early 1900's, systematic studies to demonstrate safety and efficacy began only in 1967 with the treatment of breast carcinoma. In 1975, Dougherty et al. conclusively established that long-term cure is possible with photodynamic therapy (PDT). Currently, phototherapeutic methods are also being investigated for the treatment of some cardiovascular disorders such as atherosclerosis and vascular restenosis, for the treatment of rheumatoid arthritis, and for the treatment of some inflammatory diseases such as Chron's disease.

Phototherapeutic procedures require photosensitizers (i.e. chromophores) having high absorptivity. These compounds should preferably be chemically inert and become activated only upon irradiation with light of an appropriate wavelength. Selective tissue injury can be induced with light when photosensitizers bind to the target tissues, either directly or through attachment to a bioactive carrier. Furthermore, if the photosensitizer is also a chemotherapeutic agent (e.g., anthracycline antitumor agents), then an enhanced therapeutic effect can be attained. The key requirements for the design of effective phototherapeutic agents are: (a) large molar extinction coefficients, (b) long triplet lifetimes, (c) high yields of singlet oxygen and/or other reactive intermediates, viz., free radicals, nitrenes, carbenes, or open-shell ionic species such as cabonium ions and the like, (d) efficient energy or electron transfer to cellular components, (e) low tendency to form aggregation in an aqueous milieu, (f) efficient and selective targeting of lesions, (g) rapid clearance from the blood and non-target tissues, (h) low systemic toxicity, and (i) lack of mutagenicity.

Photosensitizers operate via two distinct mechanisms, termed Types 1 and 2. The type 1 mechanism is shown in the following scheme:

Type 1 mechanisms involve direct energy or electron transfer from the photosensitizer to the cellular components thereby causing cell death. Type 2 mechanisms involve two distinct steps, as shown in the following scheme:

In the first step, singlet oxygen is generated by energy transfer from the triplet excited state of the photosensitizer to the oxygen molecules surrounding the tissues. In the second step, collision of singlet oxygen with the tissues promotes tissue damage. In both Type 1 and Type 2 mechanisms, the photoreaction proceeds via the lowest triplet state of the sensitizer. Hence, a relatively long triplet lifetime is required for effective phototherapy. In contrast, a relatively short triplet lifetime is required to avoid photodamage to the tissue caused by photosensitizers.

The biological basis of tissue injury brought about by tumor phototherapeutic agents has been the subject of intensive study. Various biochemical mechanisms for tissue damage have been postulated even though the type and number of photosensitizers employed in these studies are relatively small. These biochemical mechanisms are as follows: a) cancer cells upregulate the expression of low density lipoprotein (LDL) receptors, and photodynamic therapy (PDT) agents bind to LDL and albumin selectively; (b) porphyrin-like substances are selectively taken up by proliferative neovasculature; (c) tumors often contain increased number of lipid bodies and are thus able to bind to hydrophobic photosensitizers; (d) a combination of "leaky" tumor vasculature and reduced lymphatic drainage causes porphyrin accumulation; (e) tumor cells may have increased capabilities for phagocytosis or pinocytosis of porphyrin aggregates; (f) tumor associated macrophages may be largely responsible for the concentration of photosensitizers in tumors; and (g) cancer cells may undergo apoptosis induced by photosensitizers. Among these mechanisms, (f) and (g) are the most general and, of these two alternatives, there is a general consensus that (f) is the most likely mechanism by which the phototherapeutic effect of porphyrin-like compounds is induced.

Most of the currently known photosensitizers are commonly referred to as photodynamic therapy (PDT) agents and operate via the Type 2 mechanism. For example, Photofrin II (a hematoporphyrin derivative) has been recently approved by the United States Food and Drug Administration for the treatment of bladder, esophageal, and late-stage lung cancers. However, Photofrin II has been shown to have several drawbacks: a low molar absorptivity ($\epsilon$=3000 M$^{-1}$), a low singlet oxygen quantum yield ($\Phi$=0.1), chemical heterogeneity, aggregation, and prolonged cutaneous photosensitivity. Hence, there has been considerable effort in developing safer and more effective photosensitizers for PDT which exhibit improved light absorbance properties, better clearance, and decreased skin photosensitivity compared to Photofrin II. These include monomeric porphyrin derivatives, corrins, cyanines, phthalocyanines, phenothiazines, rhodamines, hypocrellins, and the like. However, these phototherapeutic agents mainly also operate via the Type 2 mechanism.

Surprisingly, there has not been much attention directed at developing Type 1 phototherapeutic agents, despite the fact that the Type 1 mechanism appears to be inherently more efficient than the Type 2 mechanism. First, unlike Type 2, Type 1 photosensitizers do not require oxygen for causing cellular injury. Second, the Type 1 mechanism involves two steps (photoexcitation and direct energy transfer), whereas the Type 2 mechanism involves three steps (photoexcitation, singlet oxygen generation, and energy transfer). Furthermore, certain tumors have hypoxic regions, which renders the Type 2 mechanism ineffective. However, in spite of the drawbacks associated with the Type 2 mechanism, only a small number of compounds have been developed that operate through the Type 1 mechanism, e.g. anthracyline antitumor agents.

Thus, there is a need to develop effective phototherapeutic agents that operate via the Type 1 mechanism. Phototherapeutic efficacy can be further enhanced if the excited state photosensitizers can generate reactive intermediates such as free radicals, nitrenes, carbenes, and the like, which have much longer lifetimes than the excited chromophore and have been shown to cause considerable cell injury. Thus, there is a need in the art to develop effective phototherapeutic agents. Phototherapeutic efficacy can be substantially improved if both Type 1 and Type 2 units are integrated into a single compound. This can be accomplished using three types of formulation: (a) homogeneous mixtures of Type 1 or Type 2 agents alone, (b) heterogeneous mixtures of Type 1 and Type 2 agents, or (c) single molecular entity containing both Type 1 and Type 2 functionalities.

SUMMARY OF THE INVENTION

The present invention discloses novel sulfenate derivatives and their bioconjugates for phototherapy of tumors and other lesions. The compounds have the general formula wherein E is selected from the group consisting of somatostatin, ST, neurotensin, bombesin, cholecystekinin, steroid, and carbohydrate receptor binding molecules, and dihydoxyindolecarboxylic acid. L and X are independently selected from the group consisting of —$(R^5)$NOC—, —$(R^5)$NOCCH$_2$O—, —$(R^5)$NOCCH$_2$CH$_2$O—, —OCN$(R^5)$—, —HNC(=S)NH—, and HNC(=O)NH—. DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, indolenium dyes, crellins, and hypocrellins. $R^1$ to $R^5$ are independently selected from the group comprising hydrogen, C1-C10 alkyl, C5-C10 aryl, C1-C10polyhydroxyalkyl, and C1-C10 polyalkoxyalkyl. Ar is an aromatic or heteroaromatic radical derived from the group consisting of benzenes, naphthalenes, naphthoquinones, diphenylmethanes, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines.

The present invention also discloses a method of performing a phototherapeutic procedure using the novel sulfenate derivatives and their bioconjugates. An effective amount of sulfenate photosensitizers having the formula is administered to a subject. In the formula, E is selected from the group consisting of somatostatin, ST, neurotensin, bombesin, cholecystekinin, steroid, and carbohydrate receptor binding molecules, and dihydroxyindolecarboxylic acid. L and X are independently selected from the group consisting of —$(R^5)$NOC—, —$(R^5)$NOCCH$_2$O—, —$(R^5)$NOCCH$_2$CH$_2$O—, —OCN$(R^5)$—, —HNC(=S)NH—, and HNC(=O)NH—. DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, indolenium dyes, crellins, and hypocrellins. $R^1$ to $R^5$ are independently selected from the group comprising hydrogen, C1-C10 alkyl, C5-C10 aryl, C1-C10 polyhydroxyalkyl, and C1-C10 polyalkoxyalkyl. Ar is an aromatic or heteroaromatic radical derived from the group consisting of benzenes, naphthalenes, naphthoquinones, diphenylmethanes, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines. Following the administration, the photosensitizer is allowed to accumulate in target tissue which is exposed to light of wavelength between 300 and 950 nm with sufficient power and fluence rate to cause necrosis or apoptosis of the said target tissue.

DETAILED DESCRIPTION OF THE INVENTION

The present invention discloses novel sulfenate derivatives and their bioconjugates for phototherapy of tumors and other lesions. The compounds have the general formula wherein E is either a hydrogen atom or is selected from the group comprising antibodies, peptides, peptidomimetics, carbohydrates, glycomimetics, drugs, hormones, or nucleic acids; L and X are independently selected from the group consisting of —($R^5$)NOC—, —($R^5$)NOCCH$_2$O—, —($R^5$)NOCCH$_2$CH$_2$O—, —OCN($R^5$)—, —HNC(=S)NH—, and HNC(=O)NH—; DYE is an aromatic or a heteroaromatic radical derived from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, indolenium dyes, and the like; $R^1$ to $R^5$ are independently selected from the group comprising hydrogen, C1-C10 alkyl, C5-C10 aryl, C1-C10 polyhydroxyalkyl, and C1-C10 polyalkoxyalkyl; and Ar is an aromatic or heteroaromatic radical derived from the group consisting of benzenes, naphthalenes, naphthoquinones, diphenylmethanes, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines.

In one embodiment, sulfenates according to the present invention have the general Formula 1 above, wherein E is selected from the group consisting of somatostatin, (ST), neurotensin, bombesin, cholecystekinin (CCK), steroid, and carbohydrate receptor binding molecules, and dihydroxyindolecarboxylic acid; X is selected from the group consisting of —($R^5$)NOC—, —($R^5$)NOCCH$_2$O—, —($R^5$)NOCCH$_2$CH$_2$O—, and —HNC(=S)NH; DYE is an aromatic or a heteroaromatic radical derived from the group consisting of cyanines, indocyanines, phthalocyanines, rhodamines, phenoxazines, phenothiazines, fluoresceins, porphyrins, benzoporphyrins, and indolenium dyes; $R^1$ to $R^5$ are independently selected from the group consisting of hydrogen, C1-C10 alkyl, C5-C10 aryl, and C1-C10 polyhydroxyalkyl; and Ar is an aromatic or heteroaromatic radical derived from the group consisting of benzenes, diphenylmethanes, fluorenes, anthraquinones, naphthacenediones, pyridines, quinolines, isoquinolines, indoles, acridines, acridones, phenanthridines, xanthenes, xanthones, and anthacylines.

In an alternative embodiment, sulfenates according to the present invention have the general formula above, wherein E is selected from the group consisting of somatostatin, ST, neurotensin, bombesin, cholecystekinin, steroid, and carbohydrate receptor binding molecules; X is —($R^5$)NOC—, and —($R^5$)NOCCH$_2$O—; DYE is an aromatic or a heteroaromatic radical derived from the group consisting of cyanines, phthalocyanines, rhodamines, porphyrins, benzoporphyrins, and corrins; $R^1$ to $R^5$ are independently selected from the group comprising hydrogen, and C1-C10 alkyl; and Ar is an aromatic or heteroaromatic radical derived from the group consisting of benzenes, diphenylmethanes, fluorenes, anthraquinones, naphthacenediones, pyridines, quinolines, indoles, acridines, acridones, phenanthridines, xanthenes, xanthones, and anthacylines.

Figure 1:
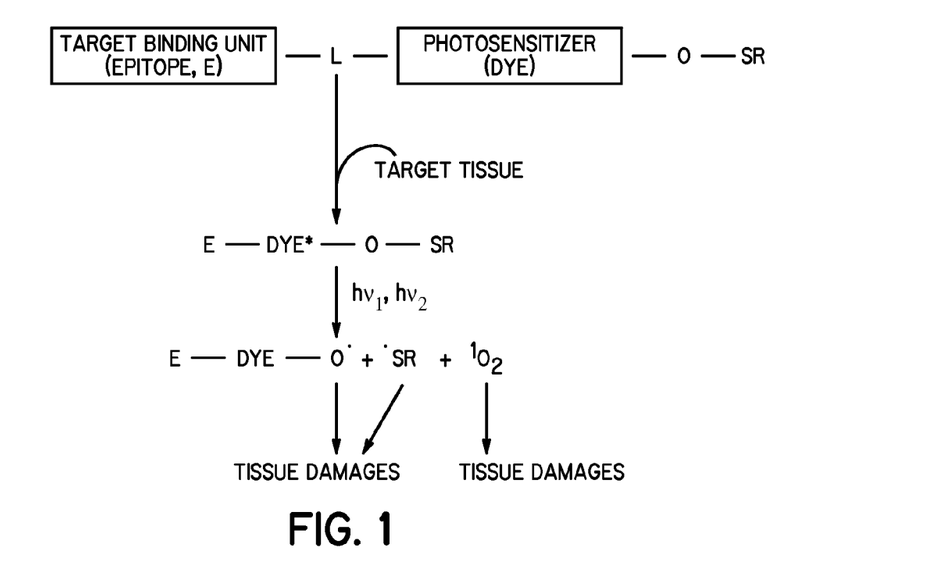
FIG. 1 is a schematic mechanism for activation of the inventive compounds.

These compounds operate mainly by Type I mechanism as shown in FIG. 1, wherein —O—SR is the sulfenate moiety that produces free radicals upon photoactivation, and Ar is an aromatic chromophore that undergoes photosensitization. Aliphatic sulfenates can also be used for phototherapy, but they are generally considered to be unstable and difficult to handle under ordinary conditions. L is a linker between the chromophore and the epitope. Epitope (E) is a particular region of the molecule that is recognized by, and binds to, the target site on the cell. An epitope is usually, but not always, associated with biomolecules which include hormones, amino acids, peptides, peptidomimetics, proteins, nucleosides, nucleotides, nucleic acids, enzymes, carbohydrates, glycomimetics, lipids, albumins, mono- and polyclonal antibodies, receptors, inclusion compounds such as cyclodextrins, and receptor binding molecules. Specific examples of biomolecules include steroid hormones for the treatment of breast and prostate lesions, somatostatin, bombesin, and neurotensin receptor binding molecules for the treatment of neuroendocrine tumors, cholecystekinin receptor binding molecules for the treatment of lung cancer, (ST) receptor, and carcinoembryonic antigen (CEA) binding molecules for the treatment of colorectal cancer, dihydroxyindolecarboxylic acid and other melanin producing biosynthetic intermediates for melanoma, integrin receptor and atherosclerotic plaque binding molecules for the treatment of vascular diseases, and amyloid plaque binding molecules for the treatment of brain lesions. Biomolecules for use in the present invention may also include synthetic polymers. Examples of synthetic polymers include polyaminoacids, polyols, polyamines, polyacids, oligonucleotides, aborols, dendrimers, and aptamers.

Coupling of diagnostic and radiotherapeutic agents to biomolecules can be accomplished by methods well known in the art, as described in Hnatowich et al., Radioactive Labeling of Antibody: A simple and efficient method. *Science*, 1983, 220, 613-615; A. Pelegrin et al., Photoimmunodiagnosis with antibody-fluorescein conjugates: in vitro and in vivo preclinical studies. *Journal of Cellular Pharmacology*, 1992, 3, 141-145; and U.S. Pat. No. 5,714,342, which are expressly incorporated by reference herein in their entireties. Successful specific targeting of fluorescent dyes to tumors using antibodies and peptides for diagnostic imaging of tumors has been demonstrated by us and others, for example, in S.A. Achilefu et al., Novel receptor-targeted fluorescent contrast agents for in vivo tumor imaging. *Investigative Radiology*, 2000, 35(8), 479-485; B. Ballou et al., Tumor labeling in vivo using cyanine-conjugated monoclonal antibodies. *Cancer Immunology and Immunotherapy*, 1995, 41, 257-263; and K. Licha et al., New contrast agents for optical imaging: acid-cleavable conjugates of cyanine dyes with biomolecules. *In Biomedical Imaging: Reporters, Dyes, and Instrumentation*, D.J. Bornhop, C. Contag, and E.M. Sevick-Muraca (Eds.), Proceedings of SPIE, 1999, 3600, 29-35, which are expressly incorporated by reference herein in their entireties. Therefore, the inventive receptor-targeted phototherapeutic agents are expected to be effective in the treatment of various lesions.

In the present invention, dual phototherapeutic effect involving both Type 1 and Type 2 mechanisms can be accomplished by incorporating the reactive intermediate precursors into conventional PDT dyes and using a dual wavelength light source to effect the generation of reactive intermediates as well as the generation of singlet oxygen. In some cases it may be possible to activate both Type 1 and Type 2 mechanisms using same wavelength of light.

In the process outlined in FIG. 1, the photoexcitation of the aromatic chromophore effects rapid intramolecular energy transfer to the sulfenate group, resulting in bond rupture and production of two reactive free radicals which cause cellular injury.

For targeting purposes, external attachment of an epitope is used. If the aromatic sulfenate compounds themselves preferentially accumulate in the target tissue, however, an additional binding group may not be needed. For example, if Ar is an anthracycline moiety, it will bind to cancer cells directly and not require an epitope for targeting purposes.

Figure 2:
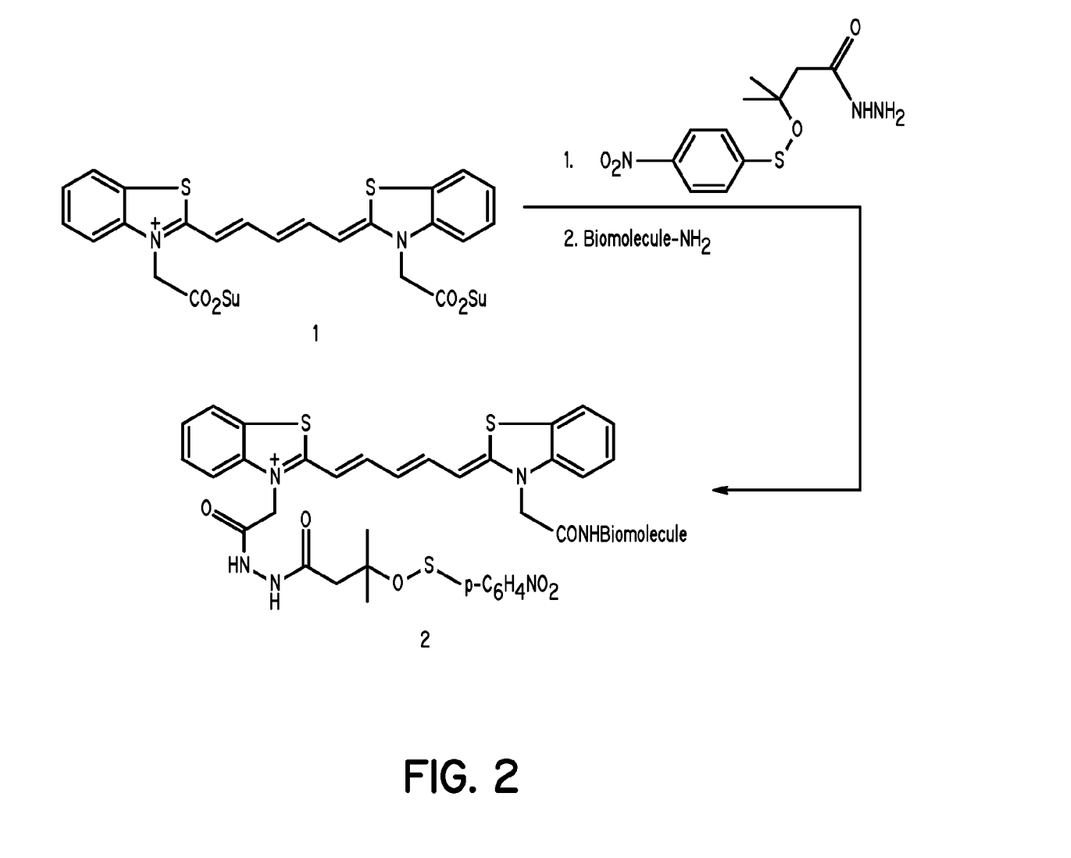
FIG. 2 is a schematic mechanism for the synthesis of a cyanine derivative.
Figure 3:
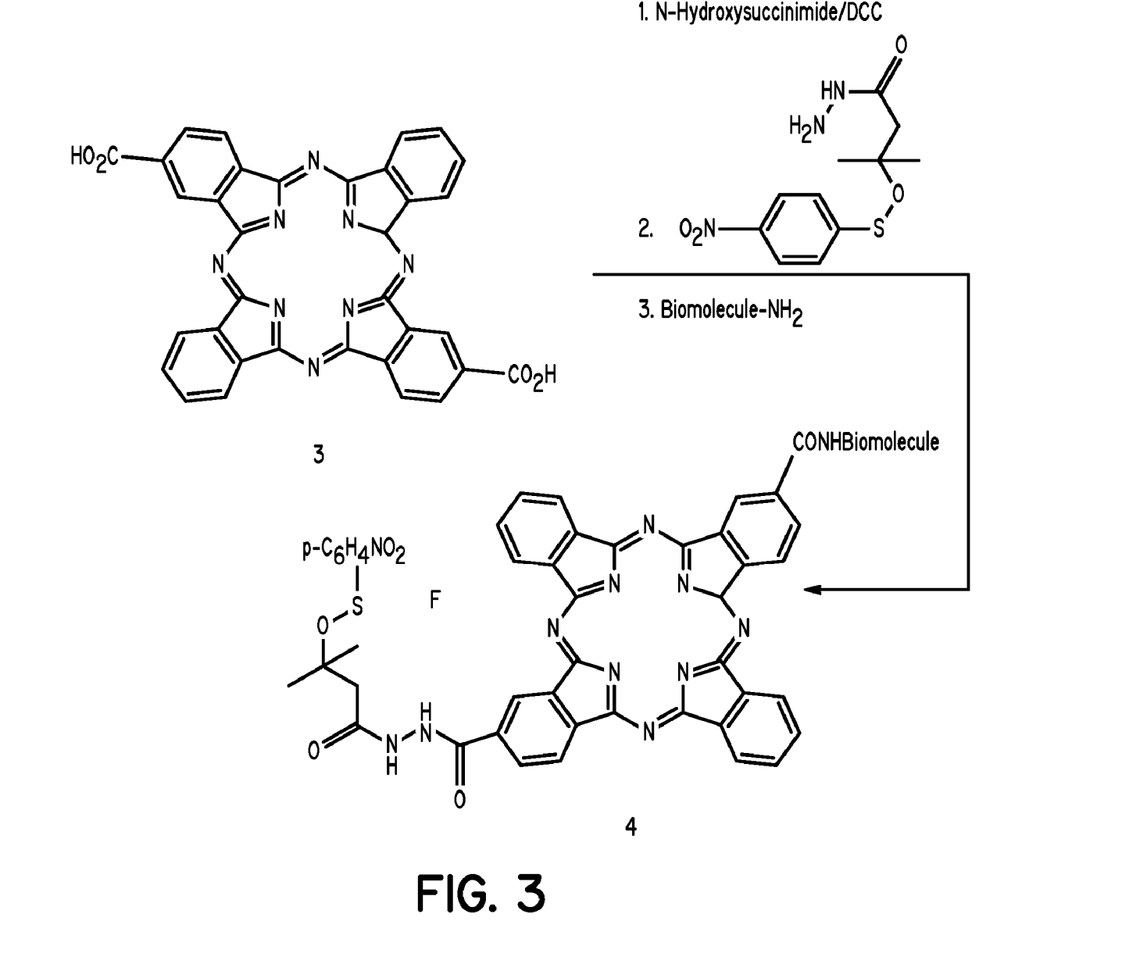
FIG. 3 is a schematic mechanism for the synthesis of a phthalocyanine derivative.

The synthesis of sulfenate derivatives is accomplished by a method which generally involves the condensation of sulfenyl chlorides with alcohols in the presence of an organic base. This method is disclosed in D.L. Pasto and F. Cottard, Demonstration of the synthetic utility of the generation of alkoxy radicals by the photo-induced, homolytic dissociation of alkyl 4-nitrobenzenesulfenates. *Tetrahedron Letters*, 1994, 35(25), 4303-4306, which is expressly incorporated by reference herein in its entirety. The dye-sulfenate derivatives of the present invention contain additional functionalities that can be used to attach various types of biomolecules, synthetic polymers, and organized aggregates for selective delivery to various organs or tissues of interest. The synthesis of typical dual phototherapeutic agents incorporating both Type 1 and Type 2 mechanisms based on cyanine and phthalocyanine derivatives are shown in FIGS. 2 and 3. One of the active esters derived from either starting acid 1, 3 can be attached to a Type 1 moiety and the other active ester can be conjugated to any desired biomolecule of interest. Specifically, the biomolecule of the present invention pertains to those binding to colorectal, cervical, ovarian, lung, and neuroendocrine tumors. These include somatostatin, cholecystekinin, bombesin, neuroendrocrine, and ST receptor binding compounds.

The novel compounds of the present invention may vary widely depending on the contemplated application. For tumors, the biomolecule is selected from the class of tumor markers including, but not limited to, somatostatin, bombesin, neurotensin, cholesytekinin, ST, estrogen, and progesterone receptor binding compounds. For vascular lesions, the biomolecule may be selected from the class of integrins, selectins, vascular endothelial growth factor, fibrins, tissue plasminogen activator, thrombin, LDL, HDL, Sialyl Lewis$^x$ and its mimics, and atherosclerotic plaque binding compounds.

Methods of performing therapeutic procedures with the inventive compounds are also disclosed. An effective amount of the inventive compound in a pharmaceutically acceptable formulation is administered to a patient. For example, parenteral administration advantageously contains a sterile aqueous solution or suspension of the photosensitizer in a concentration ranging from about 1 nM to about 0.5 M. Preferred parenteral formulations have a concentration of 1 µM to 10 mM photosensitizer. Such solutions also may contain pharmaceutically acceptable buffers, emulsifiers, surfactants, and, optionally, electrolytes such as sodium chloride. Formulations for enteral administration may vary widely, as is well known in the art. In general, such formulations are liquids, which include an effective amount of the complexes in aqueous solution or suspension. Such enteral compound may optionally include buffers, surfactants, emulsifiers, thixotropic agents, and the like. Compounds for oral administration may also contain flavoring agents and other ingredients for enhancing their organoleptic qualities. Formulations for topical delivery may also contain liquid or semisolid excipients to assist in the penetration of the photosensitizer. The compounds may also be delivered in an aerosol spray. The dose of the photosensitizer may vary from 0.1 to 500 mg/kg body weight, preferably from 0.5 to 2 mg/kg body weight. The photosensitizer is allowed to accumulate in the region of interest, followed by illumination with the light of wavelength 300 to 1200 nm, preferably 350 to 850 nm, at the site of the lesion. If the lesion is on the skin surface, the photosensitizer can be directly illuminated; otherwise, endoscopic catheters equipped with a light source may be employed to achieve phototherapeutic effect. The intensity, power, duration of illumination, and the wavelength of the light may vary widely depending on the location and site of the lesions. The wavelength of light may vary from 300 to 1200 nm. The fluence rate is preferably, but not always, kept below 200 mW/cm$^2$ to minimize thermal effects. Appropriate power depends on the size, depth, and the pathology of the lesion. The inventive compounds have broad clinical utility which includes, but is not limited to, phototherapy of tumors, inflammatory processes, and impaired vasculature.

The inventive compounds can be formulated into diagnostic or therapeutic compounds for enteral, parenteral, topical, or cutaneous administration. Topical or cutaneous delivery of the photosensitizer may also include aerosol formulation, creams, gels, solutions, etc. The compounds are administered in doses effective to achieve the desired diagnostic or therapeutic effect. Such doses may vary widely depending upon the particular complex employed, the organs or tissues to be examined, the equipment employed in the clinical procedure, the efficacy of treatment achieved, and the like. These compounds contain an effective amount of the phototherapeutic agent, along with conventional pharmaceutical carriers and excipients appropriate for the type of administration contemplated. These compounds may also include stabilizing agents and skin penetration enhancing agents.

The aforementioned examples illustrate specific embodiments of the invention. As would be apparent to skilled artisans, various changes and modifications are possible and are contemplated within the scope of the invention described. It should be understood that the embodiments of the present invention shown and described in the specification are only specific embodiments of the inventors, who are skilled in the art, and are not limiting in anyway. Therefore, various changes, modifications or alterations to those embodiments may be made or resorted to without departing from the spirit of the inventions and the scope of the following claims. For example, although the compounds of the present invention are primarily directed at therapy, most of the compounds containing polycyclic aromatic chromophores can also be used for optical diagnostic imaging purposes.

What is claimed is:

1. A compound of the formula, wherein
  E is selected from the group consisting of somatostatin receptor binding molecules, ST receptor binding molecules, neurotensin receptor binding molecules, bombesin receptor binding molecules, cholecystekinin receptor binding molecules, steroid receptor binding molecules, carbohydrate receptor binding molecules, and dihydroxyindolecarboxylic acid;

L and X are independently selected from the group consisting of —(R$^5$)NOC—, —(R$^5$)NOCCH$_2$O—, —(R$^5$)NOCCH$_2$CH$_2$O—, —OCN(R$^5$)—, —HNC(=S)NH—, and HNC(=O)NH—;

DYE is an aromatic or a heteroaromatic radical selected from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, indolenium dyes, crellins, and hypocrellins;

R$^1$ to R$^5$ are independently selected from the group comprising hydrogen, C1-C10 alkyl, C5-C10 aryl, C1-C10 polyhydroxyalkyl, and C1-C10 polyalkoxyalkyl; and Ar is an aromatic or heteroaromatic radical selected from the group consisting of benzenes, naphthalenes, naphthoquinones, diphenylmethanes, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines.

2. The compound of claim 1 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —(R$^5$)NOC—, and —(R$^5$)NOCCH$_2$O—; DYE is selected from cyanines; R$^1$ to R$^5$ are independently selected from the group consisting of hydrogen, C1-C10 alkyl, C5-C10 aryl, and C1-C10polyhydroxyalkyl; and Ar is an aromatic radical selected from benzenes.

3. The compound of claim 1 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; X is selected from the group consisting of —(R$^5$)NOC—, and —(R$^5$)NOCCH$_2$O —; DYE is selected from phthalocyanines; R$^1$ to R$^5$ are independently selected from the group consisting of hydrogen, C1-C10alkyl, C5-C10 aryl, and C1-C10 polyhydroxyalkyl; and Ar is an aromatic radical selected from benzenes.

4. The compound of claim 1 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —(R$^5$)NOC—, and —(R$^5$)NOCCH$_2$O—; DYE is selected from rhodamines; R$^1$ to R$^5$ are independently selected from the group consisting of hydrogen, C1-C10 alkyl, C5-C10 aryl, and C1-C10 polyhydroxyalkyl; and Ar is an aromatic radical selected from benzenes.

5. The compound of claim 1 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —(R$^5$)NOC—, and —(R$^5$)NOCCH$_2$O—; DYE is selected from porphyrins; R$^1$ to R$^5$ are independently selected from the group consisting of hydrogen, C1-C10 alkyl, C5-C10 aryl, and C1-C10 polyhydroxyalkyl; and Ar is an aromatic radical selected from benzenes.

6. The compound of claim 1 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —(R$^5$)NOC—, and —(R$^5$)NOCCH$_2$O—; DYE is selected from benzoporphyrins; R$^1$ to R$^5$ are independently selected from the group consisting of hydrogen, C1-C10 alkyl, C5-C10 aryl, and C1-C10 polyhydroxyalkyl; and Ar is an aromatic radical selected from benzenes.

7. The compound of claim 1 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —(R$^5$)NOC—, and —(R$^5$)NOCCH$_2$O—; DYE is selected from corrins; R$^1$ to R$^5$ are independently selected from the group consisting of hydrogen, C1-C10 alkyl, C5-C10 aryl, and C1-C10 polyhydroxyalkyl; and Ar is an aromatic radical selected from benzenes.

8. The compound of claim 1 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —(R$^5$)NOC—, and —(R$^5$)NOCCH$_2$O—; DYE is selected from phenothiazines; R$^1$ to R$^5$ are independently selected from the group consisting of hydrogen, C1-C10 alkyl, C5-C10 aryl, and C1-C10 polyhydroxyalkyl; and Ar is an aromatic radical selected from benzenes.

9. The compound of claim 1 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —(R$^5$)NOC—, and —(R$^5$)NOCCH$_2$O—; DYE is selected from hypocrellins; R$^1$ to R$^5$ are independently selected from the group consisting of hydrogen, C1-C10 alkyl, C5-C10 aryl, and C1-C10 polyhydroxyalkyl; and Ar is an aromatic radical selected from benzenes.

10. The compound of claim 1 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —(R$^5$)NOC—, and —(R$^5$)NOCCH$_2$O—; DYE is selected from fluoresceins; R$^1$ to R$^5$ are independently selected from the group consisting of hydrogen, C1-C10 alkyl, C5-C10 aryl, and C1-C10 polyhydroxyalkyl; and Ar is an aromatic radical selected from benzenes.

11. The compound of claim 1 wherein E is selected from the group consisting of hormones, amino acids, peptides, peptidomimetics, proteins, nucleosides, nucleotides, nucleic acids, enzymes, carbohydrates, glycomimetics, lipids, albumins, monoclonal antibodies, polyclonal antibodies, receptors, inclusion compounds, receptor binding molecules, polyaminoacids, polyols, polyamines, polyacids, oligonucleotides, aborols, dendrimers, and aptamers.

12. A pharmaceutically acceptable composition comprising at least one carrier or excipient and a compound of the formula, wherein
E is selected from the group consisting of somatostatin receptor binding molecules, ST receptor binding molecules, neurotensin receptor binding molecules, bombesin receptor binding molecules, cholecystekinin receptor binding molecules, steroid receptor binding molecules, carbohydrate receptor binding molecules, and dihydroxyindolecarboxylic acid;
L and X are independently selected from the group consisting of —($R^5$)NOC—, —($R^5$)NOCCH$_2$O—, —($R^5$)NOCCH,CH$_2$O—, —OCN($R^5$)—, —HNC(=S)NH—, and HNC(=O)NH—;
DYE is an aromatic or a heteroaromatic radical selected from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo dyes, methine dyes, indolenium dyes, crellins, and hypocrellins;
$R^1$ to $R^5$ are independently selected from the group comprising hydrogen, C1-C10 alkyl, C5-C10 aryl, C1-C10 polyhydroxyalkyl, and C1-C10 polyalkoxyalkyl; and
Ar is an aromatic or heteroaromatic radical selected from the group consisting of benzenes, naphthalenes, naphthoquinones, diphenylmethanes, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines.

13. The composition of claim 12 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —($R^5$)NOC—, and —($R^5$)NOCCH$_2$O—; DYE is selected from cyanines; $R^1$ to $R^5$ are independently selected from the group consisting of hydrogen, C1-C10 alkyl, C5-C10 aryl, and C1-C10 polyhydroxyalkyl; and Ar is an aromatic radical selected from benzenes.

14. The composition of claim 12 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; X is selected from the group consisting of —($R^5$)NOC—, and —($R^5$)NOCCH$_2$O—; DYE is selected from phthalocyanines; $R^1$ to $R^5$ are independently selected from the group consisting of hydrogen, C1-C10 alkyl, C5-C10 aryl, and C1-C10 polyhydroxyalkyl; and Ar is an aromatic radical selected from benzenes.

15. The composition of claim 12 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —($R^5$)NOC—, and —($R^5$)NOCCH$_2$O—; DYE is selected from rhodamines; $R^1$ to $R^5$ are independently selected from the group consisting of hydrogen, C1-C10 alkyl, C5-C10 aryl, and C1-C10 polyhydroxyalkyl; and Ar is an aromatic radical selected from benzenes.

16. The composition of claim 12 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —($R^5$)NOC—, and —($R^5$)NOCCH$_2$O—; DYE is selected from porphyrins; $R^1$ to $R^5$ are independently selected from the group consisting of hydrogen, C1-C10 alkyl, C5-C10 aryl, and C1-C10 polyhydroxyalkyl; and Ar is an aromatic radical selected from benzenes.

17. The composition of claim 12 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —($R^5$)NOC—, and —($R^5$)NOCCH$_2$O—; DYE is selected from benzoporphyrins; $R^1$ to $R^5$ are independently selected from the group consisting of hydrogen, C1-C10 alkyl, C5-C10 aryl, and C1-C10 polyhydroxyalkyl; and Ar is an aromatic radical selected from benzenes.

18. The composition of claim 12 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —($R^5$)NOC—, and —($R^5$)NOCCH$_2$O—; DYE is derived selected from corrins; $R^1$ to $R^5$ are independently selected from the group consisting of hydrogen, C1-C10 alkyl, C5-C10 aryl, and C1-C10 polyhydroxyalkyl; and Ar is an aromatic radical selected from benzenes.

19. The composition of claim 12 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —($R^5$)NOC—, and —($R^5$)NOCCH$_2$O—; DYE is derived from phenothiazines; $R^1$ to $R^5$ are independently selected from the group consisting of hydrogen, C1-C10 alkyl, C5-C10 aryl, and C1-C10 polyhydroxyalkyl; and Ar is an aromatic radical selected from benzenes.

20. The composition of claim 12 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —($R^5$)NOC—, and —($R^5$)NOCCH$_2$O—; DYE is selected from hypocrellins; $R^1$ to $R^5$ are independently selected from the group consisting of hydrogen, C1-C10 alkyl, C5-C10 aryl, and C1-C10 polyhydroxyalkyl; and Ar is an aromatic radical selected from benzenes.

21. The composition of claim 12 wherein E is selected from the group consisting of somatostatin receptor binding molecules, ST receptor binding molecules, neurotensin receptor binding molecules, bombesin receptor binding molecules, cholecystekinin receptor binding molecules, and steroid receptor binding molecules; L and X are independently selected from the group consisting of —($R^5$)NOC—, and —($R^5$)NOCCH$_2$O—; DYE is selected from fluoresceins; $R^1$ to $R^5$ are independently selected from the group consisting of hydrogen, C1-C10 alkyl, C5-C10 aryl, and C1-C10 polyhydroxyalkyl; and Ar is an aromatic radical selected from benzenes.

22. The composition of claim 12 wherein E is selected from the group consisting of hormones, amino acids, peptides, peptidomimetics, proteins, nucleosides, nucleotides, nucleic acids, enzymes, carbohydrates, glycomimetics, lipids, albumins, monoclonal antibodies, polyclonal antibodies, receptors, inclusion compounds, receptor binding molecules, polyaminoacids, polyols, polyamines, polyacids, oligonucleotides, aborols, dendrimers, and aptamers.

* * * * *

UNITED STATES PATENT AND TRADEMARK OFFICE
CERTIFICATE OF CORRECTION

PATENT NO. : 7,758,861 B2
APPLICATION NO. : 11/277057
DATED : July 20, 2010
INVENTOR(S) : Rajagopalan et al.

Page 1 of 1

It is certified that error appears in the above-identified patent and that said Letters Patent is hereby corrected as shown below:

Column 9
    Line 36, "C1 – C10polyhydroxyalkyl", should read, -- C1-C10 polyhydroxyalkyl --
    Line 46, "C1-C10alkyl", should read, -- C1-C10 alkyl --

Column 11
    Line 25, "NOCCH,CH$_2$O-", should read, -- NOCCH$_2$CH$_2$O --

Column 12
    Line 48, "DYE is derived selected", should read, -- DYE is selected --

Signed and Sealed this

Fifth Day of October, 2010

David J. Kappos
*Director of the United States Patent and Trademark Office*